United States Patent [19]

Ullman et al.

[11] Patent Number: 5,882,867
[45] Date of Patent: Mar. 16, 1999

[54] DETECTION OF NUCLEIC ACIDS BY FORMATION OF TEMPLATE-DEPENDENT PRODUCT

[75] Inventors: Edwin F. Ullman, Atherton; Linda M. Western, San Mateo; Samuel J. Rose, Los Altos, all of Calif.

[73] Assignee: Dade Behring Marburg GmbH, Marburg, Germany

[21] Appl. No.: 486,301

[22] Filed: Jun. 7, 1995

[51] Int. Cl.⁶ .............................. C12Q 1/68; C12P 19/34; C12N 15/00

[52] U.S. Cl. ................ 435/6; 435/91.2; 935/76; 935/77; 935/78

[58] Field of Search ................... 435/6, 91.2; 536/23.1, 536/24.3; 935/76, 77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 4,800,159 | 1/1989 | Mullis et al. | 435/172.3 |
| 4,851,331 | 7/1989 | Vary et al. | 435/6 |
| 4,868,104 | 9/1989 | Kurn et al. | 435/6 |
| 4,965,188 | 10/1990 | Mullis et al. | 435/6 |
| 5,008,182 | 4/1991 | Sninsky et al. | 435/5 |
| 5,354,668 | 10/1994 | Auerbach | 435/91.1 |
| 5,427,930 | 6/1995 | Birkenmeyer et al. | 435/91.52 |
| 5,455,166 | 10/1995 | Walker | 435/91.2 |
| 5,457,027 | 10/1995 | Nadeau et al. | 435/6 |
| 5,468,613 | 11/1995 | Erlich et al. | 435/6 |
| 5,523,204 | 6/1996 | Singer et al. | 435/5 |
| 5,545,540 | 8/1996 | Mian | 435/91.21 |
| 5,554,516 | 9/1996 | Kacian | 435/91.21 |
| 5,591,609 | 1/1997 | Auerbach | 435/91.21 |

FOREIGN PATENT DOCUMENTS

| | | |
|---|---|---|
| 0 295 398 A2 | 10/1990 | European Pat. Off. . |
| 0 395 398 A3 | 10/1990 | European Pat. Off. . |
| 0 517 361 A1 | 12/1992 | European Pat. Off. . |
| WO 91/17264 | 5/1991 | WIPO . |
| WO 94/01447 | 7/1993 | WIPO . |
| WO 94/03624 | 2/1994 | WIPO . |

OTHER PUBLICATIONS

Hames., "Nucleic Acid Hybridization", pp. 3–15 and 47–71, IRL Press Ltd., Oxford, England (1985).
Kuppuswamy et al., PNAS 88 :1143–1147 (1991).
Innis et al., "PCR Protocols: A Guide to Methods and Applications", pp. 3–12 (1990).
Landegren et al., Science 241 :1077–1080 (1988).
Syvanen et al., Genomics 8: 684–692 (1990).
Sommer et al., Nucleic Acids Research 17(16): 6749 (1989).
The Stratagene Catalog, p. 39 (1988).
Walker, T., PCR Methods and Applications 3: 1–6 (1993).
Saiki, et al., Science, vol. 230: pp. 1350–1354 (Dec. 1985), "Enzymatic Amplification of β–Globin Genomic Sequences and Restriction Site Analysis for Diagnosis of Sickle Cell Anemia".
Saiki, et al., Science, vol. 239: pp. 487–491 (Jan. 1988), "Primer–Directed Enzymatic Amplification of DNA with a Thermostable DNA Polymerase".

Primary Examiner—W. Gary Jones
Assistant Examiner—Ethan Whisenant
Attorney, Agent, or Firm—Theodore J. Leitereg

[57] ABSTRACT

A method is disclosed for detecting a target polynucleotide sequence. The method comprises incubating an oligonucleotide with the target polynucleotide sequence and a nucleotide polymerase under isothermal conditions wherein at least one nucleotide is added to the 3'-terminus of the oligonucleotide to provide an extended oligonucleotide having the additional nucleotides. The presence of extended oligonucleotide is detected as an indication of the presence of the target polynucleotide sequence. The method has particular application to the detection of DNA.

23 Claims, 3 Drawing Sheets

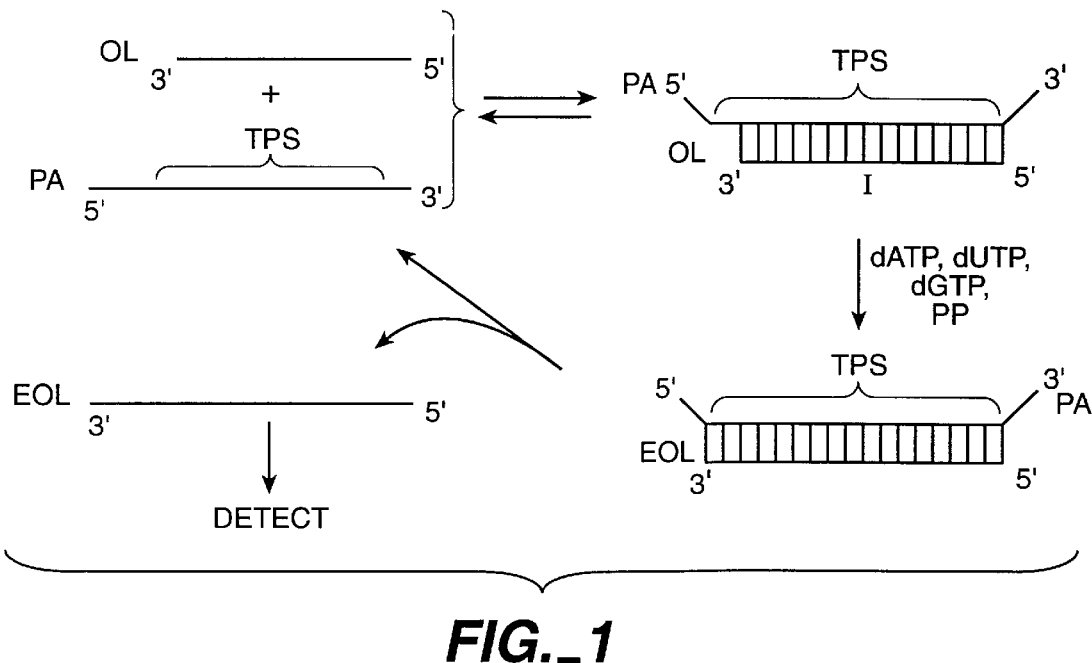
FIG._1
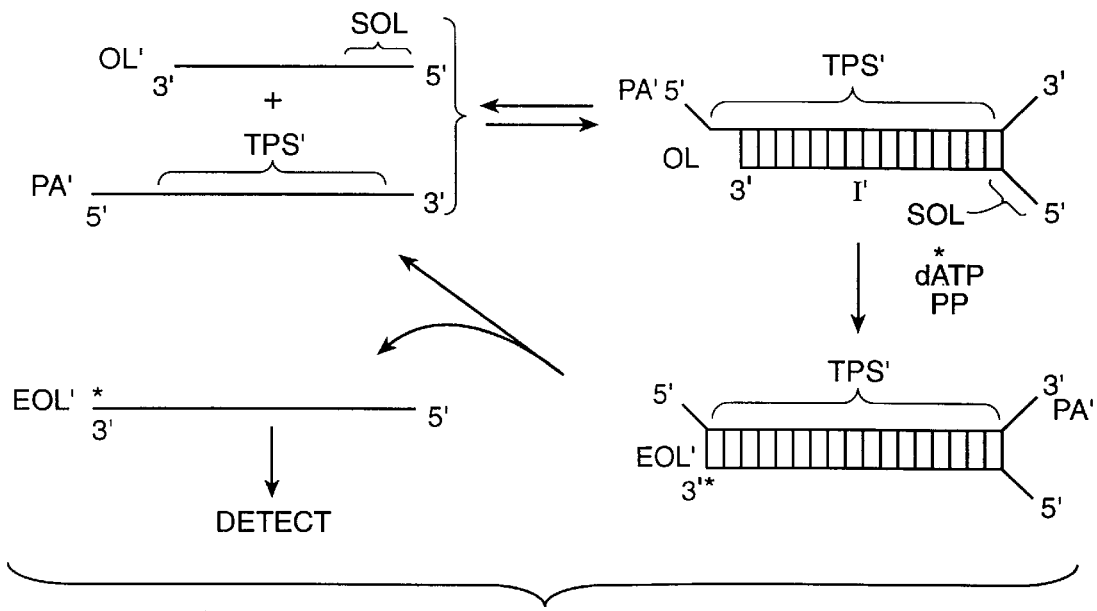
FIG._2

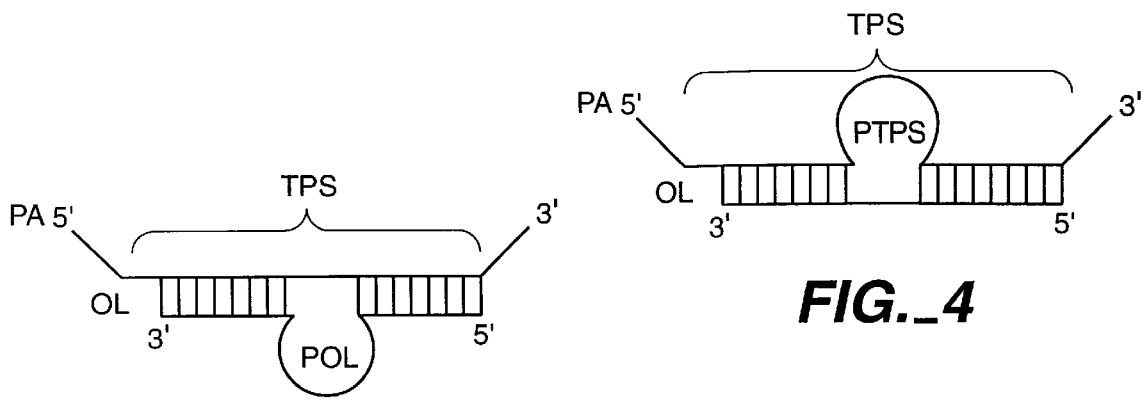
FIG._3
FIG._4
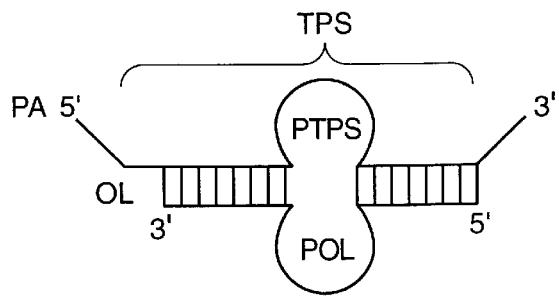
FIG._5
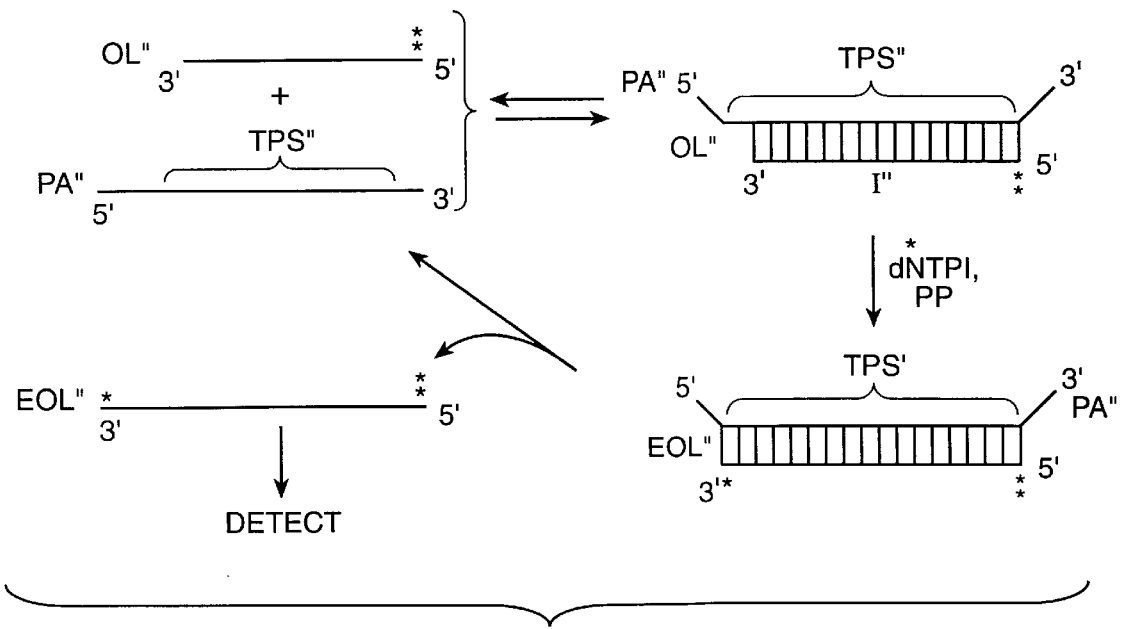
FIG._6

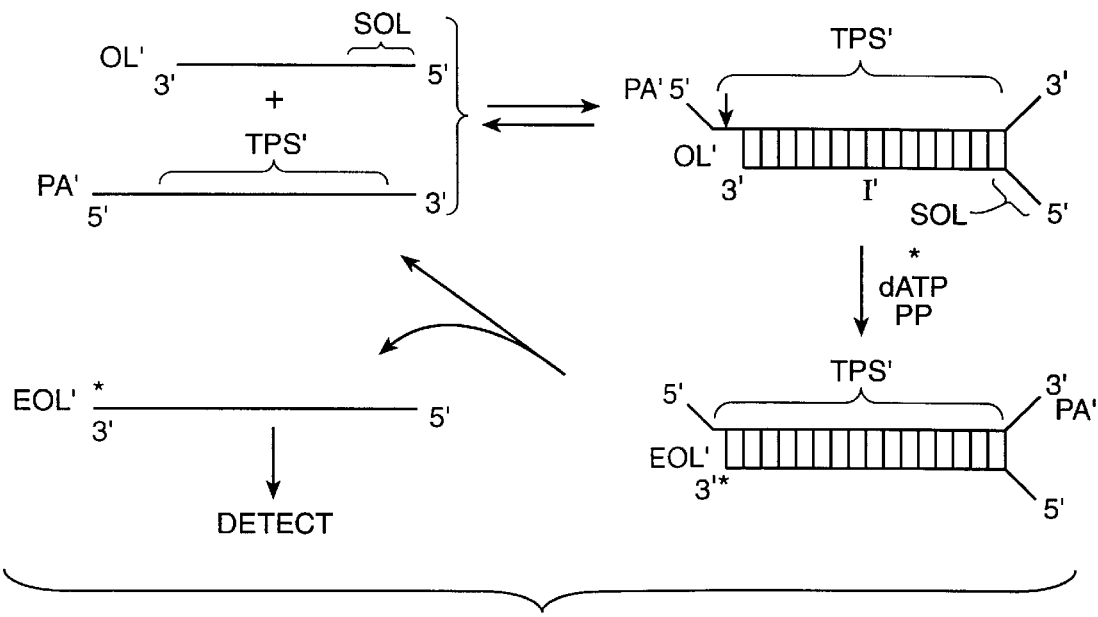
FIG._7
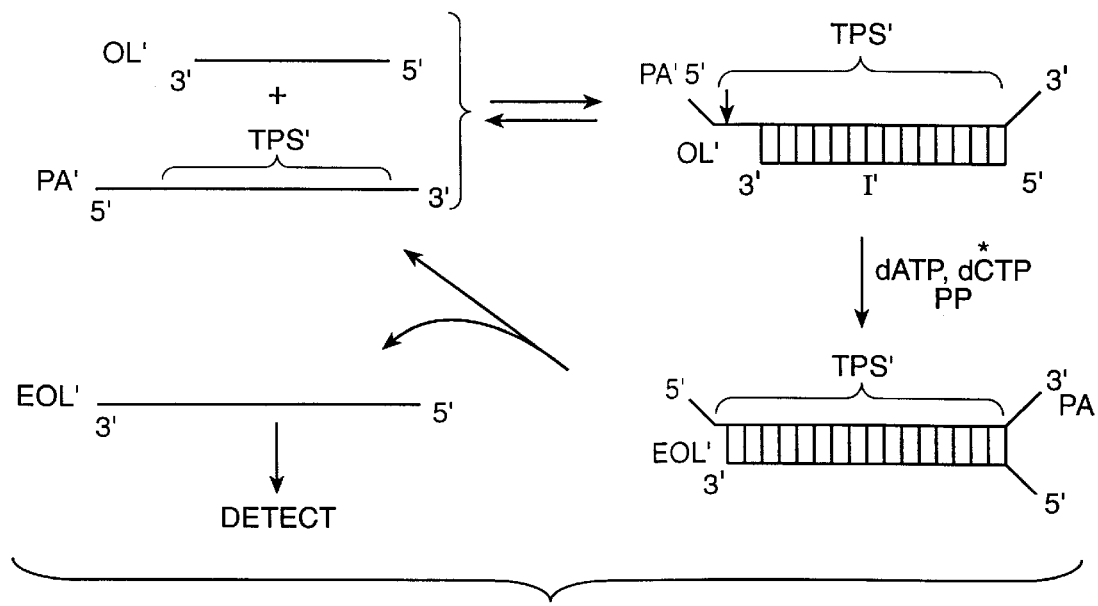
FIG._8

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:1:

GACGGCCAGT GAATTCGAGC 20

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:2:

GACGGCCAGT GAATTCGAGC T                                                                                                       21

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:3:

TCACGACGTT GTAAAACGAC GGCCACTGAA                                                                                              30

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:4:

CGTGGGAACA AACGGCGGAT                                                                                                         20

DETECTION OF NUCLEIC ACIDS BY FORMATION OF TEMPLATE-DEPENDENT PRODUCT

BACKGROUND OF THE INVENTION

1. Field of the Invention

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 polynucleotide kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

Current methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the current methods are slow and labor intensive, and nonisotopic labels that are less readily detected than radiolabels are frequently not suitable. A method for increasing the sensitivity to permit the use of simple, rapid, nonisotopic, homogeneous or heterogeneous methods for detecting nucleic acid sequences is therefore desirable.

Recently, a method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

Other methods for amplifying nucleic acids are single primer amplification, ligase chain reaction (LCR), nucleic acid sequence based amplification (NASBA) and the Q-beta-replicase method. Regardless of the amplification used, the amplified product must be detected.

Depending on which of the above amplification methods are employed, the methods generally employ from 7 to 12 or more reagents. Furthermore, the above methods provide for exponential amplification of a target or a reporter oligonucleotide. Accordingly, it is necessary to rigorously avoid contamination of assay solutions by the amplified products to avoid false positives. Some of the above methods require expensive thermal cycling instrumentation and additional reagents and sample handling steps are needed for detection of the amplified product.

Most assay methods that do not incorporate exponential amplification of a target DNA avoid the problem of contamination, but they are not adequately sensitive or simple. Some of the methods involve some type of size discrimination such as electrophoresis, which adds to the complexity of the methods.

One method for detecting nucleic acids is to employ nucleic acid probes. One method utilizing such probes is described in U.S. Pat. No. 4,868,104, the disclosure of which is incorporated herein by reference. A nucleic acid probe may be, or may be capable of being, labeled with a reporter group or may be, or may be capable of becoming, bound to a support.

Detection of signal depends upon the nature of the label or reporter group. If the label or reporter group is an enzyme, additional members of the signal producing system include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule, the medium can be irradiated and the fluorescence determined. Where the label is a radioactive group, the medium can be counted to determine the radioactive count.

It is desirable to have a sensitive, simple method for detecting nucleic acids. The method should minimize the number and complexity of steps and reagents. The need for sterilization and other steps needed to prevent contamination of assay mixtures should be avoided.

2. Description of the Related Art

High-level expression, purification and enzymatic characterization of full-length *Thermus aquaticus* DNA polymerase and a truncated form deficient in 5' to 3' exonuclease activity is discussed by Lawyer, et al., in *PCR Methods and Applications* (1993) 2:275–287.

A process for amplifying, detecting and/or cloning nucleic acid sequences is disclosed in U.S. Pat. Nos. 4,683,195, 4,683,202, 4,800,159, 4,965,188 and 5,008,182. Sequence polymerization by polymerase chain reaction is described by Saiki, et al., (1986) *Science*, 230: 1350–1354. Primer-directed enzymatic amplification of DNA with a thermostable DNA polymerase is described by Saiki, et al., *Science* (1988) 239:487.

U.S. patent applications Ser. Nos. 07/299,282 and 07/399,795, filed Jan. 19, 1989, and Aug. 29, 1989, respectively, describe nucleic acid amplification using a single polynucleotide primer. The disclosures of these applications are incorporated herein by reference including the references listed in the sections entitled "Description of the Related Art."

SUMMARY OF THE INVENTION

One embodiment of the present invention relates to a method for detecting a target polynucleotide sequence. An oligonucleotide is reversibly hybridized with a target polynucleotide sequence in the presence of a nucleotide polymerase under isothermal conditions. The target polynucleotide sequence serves as a template for addition of at least one nucleotide to the 3'-terminus of the oligonucleotide to provide an extended oligonucleotide. At least a 100-fold molar excess of the extended oligonucleotide is obtained relative to the molar amount of the target polynucleotide sequence. The presence of extended oligonucleotide is detected and indicates the presence of the target polynucleotide sequence.

Another embodiment of the present invention again relates to a method for detecting a target polynucleotide sequence. A combination is provided, which comprises a medium suspected of containing the target polynucleotide sequence, a molar excess, relative to the suspected concentration of the target polynucleotide sequence, of an oligonucleotide capable of hybridizing with the target polynucleotide sequence, 1 to 3 nucleoside triphosphates and a nucleotide polymerase. The target polynucleotide sequence and the oligonucleotide are reversibly hybridized under isothermal conditions wherein the oligonucleotide is extended at its 3'-end to produce an amount of an extended oligonucleotide that is at least 100 times the molar amount of the target polynucleotide sequence. The presence of the extended oligonucleotide is determined as an indication of the presence of the target polynucleotide sequence.

Another embodiment of the present invention is a method for detecting a DNA analyte. The method comprises providing in combination a medium suspected of containing the DNA analyte, an oligonucleotide capable of hybridizing with the DNA analyte, 1 to 3 nucleoside triphosphates and a template dependent DNA polymerase. The DNA analyte and the oligonucleotide are reversibly hybridized under isothermal conditions and the oligonucleotide is extended at its 3'-terminus to produce at least a 100-fold excess, relative to the DNA analyte, of an extended oligonucleotide. The presence of extended oligonucleotide indicates the presence of the DNA analyte.

Another embodiment of the present invention relates to a method for detecting the presence of a target polynucleotide sequence. In the method at least a 100-fold excess, relative to the target polynucleotide sequence, of an extended oligonucleotide having at least two labels is formed in relation to the presence of the target polynucleotide sequence. During the above forming an oligonucleotide is reversibly hybridized under isothermal conditions with the target polynucleotide sequence wherein the target polynucleotide sequence serves as a template for addition of at least one nucleotide to the 3'-terminus of the oligonucleotide to provide an extended oligonucleotide. One of the labels is part of one of the nucleotides and the other of the labels is part of the oligonucleotide. Both labels are detected in the extended oligonucleotide as an indication of the presence of the extended oligonucleotide, the presence thereof indicating the presence of the target polynucleotide sequence.

Another embodiment of the present invention relates to a method of forming an oligonucleotide having at least two labels. The method comprises providing in combination a catalytic amount of a target polynucleotide, a nucleotide polymerase, a first-labeled deoxynucleoside triphosphate, and a second-labeled oligonucleotide that is complementary to at least a portion of the target polynucleotide. The combination is treated under isothermal conditions such that the labeled oligonucleotide reversibly hybridizes to the target polynucleotide to form a duplex and the labeled deoxynucleoside triphosphate becomes linked to the labeled oligonucleotide.

Another aspect of the present invention is a kit for detection of a polynucleotide. The kit comprises in packaged combination (a) 1 to 3 nucleoside triphosphates at least one of which is labeled, (b) a labeled oligonucleotide complementary at its 3'-end to the polynucleotide, (c) a nucleotide polymerase, and (d) means for detection of the nucleotide triphosphate label when said label is bound to said oligonucleotide.

Another embodiment of the present invention is a method for detecting a mutation in a target polynucleotide sequence. In the method an oligonucleotide is reversibly hybridized with a target polynucleotide sequence suspected of having a mutation in the presence of a nucleotide polymerase under isothermal conditions. The target polynucleotide sequence serves as a template for addition of at least one nucleotide to the 3'-terminus of the oligonucleotide to provide an extended oligonucleotide wherein at least a 100-fold molar excess of the extended oligonucleotide is obtained relative to the molar amount of the target polynucleotide sequence. One of the nucleotides contains a label. The presence of the label in the extended oligonucleotide is determined, the presence thereof indicating the presence of the mutation in the target polynucleotide sequence.

BRIEF DESCRIPTION OF THE DRAWINGS

FIGS. 1–8 are schematics of different embodiments in accordance with the present invention.

DESCRIPTION OF THE SPECIFIC EMBODIMENTS

The present invention permits linear amplification of an oligonucleotide corresponding to, i.e., complementary to, a portion of a polynucleotide analyte otherwise referred to as a target polynucleotide sequence. As such, the methods of the present invention provide for very high sensitivity assays for polynucleotide analytes. The methods are simple to conduct and no temperature cycling is required. Consequently, no expensive thermal cycling instrumentation is needed. Furthermore, only a few reagents are used, thus further minimizing cost and complexity of an assay. No separate step is required for detection of amplified product. In addition, it is not necessary to rigorously avoid contamination of assay solutions by amplified products to avoid false positives.

In its broadest aspect the present invention provides for detecting a target polynucleotide sequence. An oligonucleotide is reversibly hybridized with a target polynucleotide sequence in the presence of a nucleotide polymerase under isothermal conditions. The target polynucleotide sequence serves as a template for addition of at least one nucleotide to the 3'-terminus of the oligonucleotide to provide an extended oligonucleotide. At least a 100-fold molar excess of the extended oligonucleotide is obtained relative to the molar amount of the target polynucleotide sequence. The presence of extended oligonucleotide is detected and indicates the presence of the target polynucleotide sequence.

Before proceeding further with a description of the specific embodiments of the present invention, a number of terms will be defined.

Polynucleotide analyte—a compound or composition to be measured that is a polymeric nucleotide. The polynucleotide analyte can contain 106 or more nucleotides, but usually will be a smaller fragment that can have about 10 to 500,000 or more nucleotides, usually about 20 to 200,000 nucleotides. The polynucleotide analytes include nucleic acids and fragments thereof from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

Microorganisms of interest include:

Corynebacteria

*Corynebacterium diphtheria*
Pneumococci

*Diplococcus pneumoniae*
Streptococci

*Streptococcus pyrogenes*
*Streptococcus salivarus*
Staphylococci

*Staphylococcus aureus*
*Staphylococcus albus*
Neisseria

*Neisseria meningitidis*
*Neisseria gonorrhea*
Enterobacteriaciae

| | |
|---|---|
| *Escherichia coli* | |
| *Aerobacter aerogenes* | The colliform |
| *Klebsiella pneumoniae* | bacteria |
| *Salmonella typhosa* | |
| *Salmonella choleraesuis* | The Salmonellae |
| *Salmonella typhimurium* | |
| *Shigella dysenteria* | |
| *Shigella schmitzii* | |
| *Shigella arabinotarda* | |
| | The Shigellae |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |
| Hemophilus-Bordetella group | *Rhizopus oryzae* |
| *Hemophilus influenza, H. ducryi* | *Rhizopus arrhizua* Phycomycetes |
| *Hemophilus hemophilus* | *Rhizopus nigricans* |
| *Hemophilus aegypticus* | *Sporotrichum schenkii* |
| *Hemophilus parainfluenza* | *Flonsecaea pedrosoi* |
| *Bordetella pertussis* | *Fonsecacea compact* |
| Pasteurellae | *Fonsecacea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |

TABLE I-continued

Microorganisms of interest include:

| | |
|---|---|
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | Herpes simplex |
| *Clostridium histolyticum* | Varicella (Chicken pox) |
| *Clostridium tertium* | Herpes Zoster (Shingles) |
| *Clostridium bifermentans* | Virus B |
| *Clostridium sporogenes* | Cytomegalovirus |
| Mycobacteria | Pox Viruses |
| *Mycobacterium tuberculosis hominis* | Variola (smallpox) |
| *Mycobacterium bovis* | Vaccinia |
| *Mycobacterium avium* | *Poxvirus bovis* |
| *Mycobacterium leprae* | Paravaccinia |
| *Mycobacterium paratuberculosis* | *Molluscum contagiosum* |
| Actinomycetes (fungus-like bacteria) | Picornaviruses |
| *Actinomyces Isaeli* | Poliovirus |
| *Actinomyces bovis* | Coxsackievirus |
| *Actinomyces naeslundii* | Echoviruses |
| *Nocardia asteroides* | Rhinoviruses |
| *Nocardia brasiliensis* | Myxoviruses |
| The Spirochetes | Influenza(A, B, and C) |
| *Treponema pallidum Spirillum minus* | Parainfluenza (1–4) |
| *Treponema pertenue Streptobacillus monoiliformis* | Mumps Virus |
| | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* | Respiratory Syncytial Virus |
| Trypanasomes | Rubella Virus |
| Mycoplasmas | Arboviruses |
| *Mycoplasma pneumoniae* | |
| Other pathogens | Eastern Equine Eucephalitis Virus |
| *Listeria monocytogenes* | Western Equine Eucephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis noA-nonB Virus |
| Chlamydia agents (naming uncertain) | Tumor Viruses |

TABLE I-continued

Microorganisms of interest include:

| Fungi | |
|---|---|
| | Rauscher Leukemia Virus |
| Cryptococcus neoformans | Gross Virus |
| Blastomyces dermatidis | Maloney Leukemia Virus |
| Hisoplasma capsulatum | |
| Coccidioides immitis | Human Papilloma Virus |
| Paracoccidioides brasiliensis | |
| Candida albicans | |
| Aspergillus fumigatus | |
| Mucor corymbifer (Absidia corymbifera) | |

Also included are genes, such as hemoglobin gene for sickle-cell anemia, cystic fibrosis gene, oncogenes, cDNA, and the like.

The polynucleotide analyte, where appropriate, may be treated to cleave the analyte to obtain a fragment that contains a target polynucleotide sequence, for example, by shearing or by treatment with a restriction endonuclease or other site specific chemical cleavage method. However, it is an advantage of the present invention that the polynucleotide analyte can be used in its isolated state without further cleavage.

For purposes of this invention, the polynucleotide analyte, or a cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90°–100° C. for a period of about 1 to 10 minutes to produce denatured material.

End of an oligonucleotide—as used herein this phrase refers to one or more nucleotides, including the terminal nucleotide, at either the 3'- or 5'-opposing sides of an oligonucleotide.

Terminus of an oligonucleotide—as used herein this term refers to the terminal nucleotide at either the 3'- or 5'-end of an oligonucleotide.

Target polynucleotide sequence—a sequence of nucleotides to be identified, which may be the polynucleotide analyte but is usually existing within one strand of a polynucleotide analyte of 10 to 100,000 or more nucleotides, usually about 20 to 50,000 nucleotides, more frequently 20 to 20,000 nucleotides. The sequence may be a continuous sequence or comprised of two discontinuous sequences on the same strand separated by one to about 50 nucleotides. The target polynucleotide sequence may contain a mutation such as a point or single nucleotide mutation, the detection of which is desired. The identity of the target polynucleotide sequence is known to an extent sufficient to allow preparation of an oligonucleotide necessary for conducting an amplification of the sequence, and will usually be completely known and be about 10–100 nucleotides, preferably 15–50 nucleotides, in length. In general, in the present method the terminus of an oligonucleotide is "modified" as follows: The oligonucleotide hybridizes to the target polynucleotide sequence and, thus, the target polynucleotide sequence acts as a template for addition of nucleotides to the 3'-terminus of the oligonucleotide, thereby yielding an "extended oligonucleotide." The oligonucleotide initially hybridizes with all of the target polynucleotide sequence, except for about 1 to 10 target nucleotides that are 5' of the site of hybridization. The initially unhybridized portion of the target polynucleotide sequence serves as the template for extension of the oligonucleotide and the portion along which the oligonucleotide extends is usually 1 to 10 nucleotides, frequently 1 to 5, preferably 1 to 3 nucleotides, in length. Accordingly, 1 to 10 nucleotides, preferably, 1 to 5 nucleotides, more preferably, 1, 2 or 3 nucleotides, are added to oligonucleotide. If the detection of a mutation is desired, the mutation lies within the 1 to 10 nucleotides referred to above, more preferably, at the first nucleotide of the template not hybridized with the oligonucleotide. The target polynucleotide sequence is a part of the polynucleotide analyte and, as mentioned above, may be the entire polynucleotide analyte.

The minimum number of nucleotides in the target polynucleotide sequence is selected to assure that the presence of target polynucleotide sequence in a sample is a specific indicator of the presence of polynucleotide analyte in a sample. Very roughly, the sequence length is usually greater than about 1.6 log L nucleotides where L is the number of base pairs in the genome of the biologic source of the sample. The maximum number of nucleotides in the target sequence is normally governed by the requirement that the oligonucleotide must be partially bound and partially unbound to the target sequence during formation of the extended oligonucleotide. If the target sequence is too long, usually greater than about 50 nucleotides, the temperature needed to achieve this condition would exceed the temperature at which currently available polymerases are active.

Oligonucleotide—a polynucleotide, usually a synthetic polynucleotide, usually single stranded and selected in view of a known (target polynucleotide) sequence of a polynucleotide analyte. The oligonucleotide(s) are usually comprised of a sequence of at least 10 nucleotides, preferably, 10 to 80 nucleotides, more preferably, 15 to 50 nucleotides.

The oligonucleotide is comprised of a first sequence of about 8 to 30 nucleotides terminating at the 3' end of the oligonucleotide that is complementary to at least a portion of target polynucleotide sequences. A second sequence of 1 to about 50 nucleotides can optionally be attached to the 5' end of the first sequence wherein a portion of the second sequence may be hybridizable with a portion of the target polynucleotide sequence.

Various techniques can be employed for preparing an oligonucleotide or other polynucleotide utilized in the present invention. They can be obtained by biological synthesis or by chemical synthesis. For short oligonucleotides (up to about 100 nucleotides) chemical synthesis will frequently be more economical as compared to biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide sequence. The oligonucleotides can be synthesized by standard methods such as those used in commercial automated nucleic acid synthesizers. Chemical synthesis of DNA on a suitably modified glass or resin results in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol*, 101, 20–78.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

Other chemical methods of polynucleotide or oligonucleotide synthesis include phosphotriester and phosphodiester methods (Narang, et al., Meth. Enzymol (1979) 68: 90) and synthesis on a support (Beaucage, et al., Tetrahedron (1981) Letters 22: 1859–1862) as well as phosphoramidate techniques, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Catalytic amount—as applied to the present invention the term catalytic amount means an amount of target polynucleotide sequence that serves as a template for modifying a larger amount, usually 10 to $10^4$ times as much of an oligonucleotide referred to above. The catalytic amount is generally about 1 to $10^9$, preferably 1 to $10^6$, copies of the target polynucleotide sequence.

Isothermal conditions—a uniform or constant temperature at which the modification of the oligonucleotide in accordance with the present invention is carried out. The temperature is chosen so that the duplex formed by hybridizing the oligonucleotide to a polynucleotide with a target polynucleotide sequence is in equilibrium with the free or unhybridized oligonucleotide and free or unhybridized target polynucleotide sequence, a condition that is otherwise referred to herein as "reversibly hybridizing" the oligonucleotide with a polynucleotide. Normally, at least 1%, preferably 20 to 80%, usually less than 95% of the polynucleotide is hybridized to the oligonucleotide under the isothermal conditions. Accordingly, under isothermal conditions there are molecules of polynucleotide that are hybridized with the oligonucleotide, or portions thereof, and are in dynamic equilibrium with molecules that are not hybridized with the oligonucleotide. Some fluctuation of the temperature may occur and still achieve the benefits of the present invention. The fluctuation generally is not necessary for carrying out the methods of the present invention and usually offer no substantial improvement.

Accordingly, the term "isothermal conditions" includes the use of a fluctuating temperature, particularly random or uncontrolled fluctuations in temperature, but specifically excludes the type of fluctuation in temperature referred to as thermal cycling, which is employed in some known amplification procedures, e.g., polymerase chain reaction. Normally the average temperature will be 25° to 95° C., preferably 40° to 85° C., more preferably 60° to 80° C.

The isothermal conditions include reversibly hybridizing an oligonucleotide with a target polynucleotide sequence at a constant temperature between 40° and 80° C. with a variance of less than ±2° C. Generally, the isothermal temperature is arrived at empirically by carrying out the present method at different temperatures and determining the optimum temperature resulting in the greatest amplification in accordance with the present invention. Computer models may also be used to select the appropriate temperature. A combination of the above may also be employed.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine(A), guanine(G), inosine, and derivatives and analogs thereof. The pyrimidine bases include cytosine (C), thymine (T), uracil (U), and derivatives and analogs thereof. Nucleoside triphosphates include deoxyribonucleoside triphosphates such as dATP, dCTP, dGTP and dTTP and ribonucleoside triphosphates such as rATP, rCTP, rGTP refers to one or more nucleotides, including the terminal and rUTP. The term "nucleoside triphosphates" also includes derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

Nucleotide—a base-sugar-phosphate combination that is the monomeric unit of nucleic acid polymers, i.e., DNA and RNA.

Modified nucleotide—is the unit in a nucleic acid polymer that results from the incorporation of a modified nucleoside triphosphate during template dependent enzyme catalyzed addition to an oligonucleotide and therefore becoming part of the nucleic acid polymer.

Nucleoside—is a base-sugar combination or a nucleotide lacking a phosphate moiety.

Nucleotide polymerase—a catalyst, usually an enzyme, for forming an extension of an oligonucleotide along a DNA template where the extension is complementary thereto. The nucleotide polymerase is a template dependent polynucleotide polymerase or "modifying enzyme" and utilizes nucleoside triphosphates as building blocks for extending the 3'-end of a oligonucleotide to provide a sequence complementary with the single stranded portion of the polynucleotide to which the oligonucleotide is hybridized to form a duplex. Usually, the catalysts are enzymes, such as DNA polymerases, for example, prokaryotic DNA polymerase (I, II, or III), T4 DNA polymerase, T7 DNA polymerase, Klenow fragment, and reverse transcriptase, preferably thermally stable enzymes such as Vent DNA polymerase, Vent$_R$ DNA polymerase, Pfu DNA polymerase, Taq DNA polymerase, and the like, derived from any source such as cells, bacteria, such as E. coli, plants, animals, virus, thermophilic bacteria, and so forth. Where the polynucleotide or target polynucleotide sequence is RNA, reverse transcriptase would be included to facilitate extension of the oligonucleotide along the polynucleotide or target polynucleotide sequence. Preferred nucleotide polymerases have substantially no 3'-exonuclease activity either in the natural state or when modified by recombinant DNA techniques to eliminate 3'-exonuclease activity, generally referred to as "exo-" or "exo minus." In the context of this invention the nucleotide polymerase has substantially no 3'-exonuclease activity when the level of such activity is such as to have no influence on the ability of the present invention to achieve its goal of adding at least one nucleotide to the oligonucleotide under isothermal conditions.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Homologous or substantially identical—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Copy—means a sequence that is a direct identical or homologous copy of a single stranded polynucleotide sequence as differentiated from a sequence that is complementary to the sequence of such single stranded polynucleotide.

Member of a specific binding pair ("sbp member")—one of two different molecules, having an area on the surface or in a cavity which specifically binds to, and is thereby defined as complementary with, a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support or may itself be a label.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label or reporter group or reporter molecule—a member of a signal producing system. Usually the label or reporter group or reporter molecule is conjugated to, i.e., is part of, an oligonucleotide, a nucleoside triphosphate or becomes bound thereto and is capable of being detected directly or, through a specific binding reaction, and can produce a detectible signal. In general, any label that is detectable can be used. The label can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectible group, and the like. Labels include an oligonucleotide or specific polynucleotide sequence that can provide a template for amplification or ligation or act as a ligand such as for a repressor protein. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence (and thus the nucleotide sequence is convertible to a label). The label can be a specific polynucleotide sequence within a nucleotide sequence and thus is comprising a label. When the label is bound to a nucleotide triphosphate it will preferably be small, usually less than 1000 daltons, preferably less than 400 daltons.

Signal Producing System—The signal producing system may have one or more components, at least one component being the label or reporter group or reporter molecule. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to, or part of, a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination.

The signal-producing system is described more fully in U.S. patent application Ser. No. 07/555,323, filed Jul. 19, 1990, the relevant disclosure of which is incorporated herein by reference.

Amplification of nucleic acids or polynucleotides—any method that results in the formation of one or more copies or complements of a nucleic acid or a polynucleotide molecule, usually a nucleic acid or polynucleotide analyte present in a medium.

Exponential amplification of nucleic acids or polynucleotides—any method that results in the formation of one or more copies of a nucleic acid or polynucleotide molecule, usually a nucleic acid or polynucleotide analyte, present in a medium.

One such method for the enzymatic amplification of specific double stranded sequences of DNA is known as the polymerase chain reaction (PCR), as described above. This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification is also mentioned above and involves exponential amplification of a single stranded polynucleotide using a single polynucleotide primer. The single stranded polynucleotide that is to be amplified contains two non-contiguous sequences that are complementary to one another and, thus, are capable of hybridizing together to form a stem-loop structure. This single stranded polynucleotide may already be part of a polynucleotide analytes or may be created as the result of the presence of a polynucleotide.

Another method for achieving the result of an amplification of nucleic acids is known as the ligase chain reaction (LCR). This method uses a ligase enzyme to join preformed nucleic acid probes. The probes hybridize with the nucleic acid analyte, if present, and ligase is employed to link the probes together resulting in two templates that can serve in the next cycle to reiterate the particular nucleic acid sequence in exponential fashion.

Another method for achieving a nucleic acid amplification is the nucleic acid sequence based amplification (NASBA). This method is promoter-directed, enzymatic process that induces in vitro continuous, homogeneous and isothermal amplification of specific nucleic acid.

Another method for amplifying a specific group of nucleic acids is the Q-beta-replicase method, which relies on the ability of Q-beta-replicase to amplify its RNA substrate exponentially.

Another method for conducting an amplification of nucleic acids is referred to as strand displacement amplification (SDA). SDA is an isothermal, in vitro DNA amplification technique based on the ability of a restriction enzyme to nick the unmodified strand of a hemiphosphorothioate form of its restriction site and the ability of a DNA polymerase to initiate replication at the nick and displace the downstream nontemplate strand intact. Primers containing the recognition sites for the nicking restriction enzyme drive the exponential amplification.

Another amplification procedure for amplifying nucleic acids is known as 3SR, which is an RNA specific target method whereby RNA is amplified in an isothermal process combining promoter directed RNA polymerase, reverse transcriptase and RNase H with target RNA.

Conditions for carrying out an amplification, thus, vary depending upon which method is selected. Some of the methods such as PCR utilize temperature cycling to achieve denaturation of duplexes, oligonucleotide primer annealing, and primer extension by thermophilic template dependent polynucleotide polymerase. Other methods such as NASBA, Q-beta-replicase method, SDA and 3SR are isothermal. As can be seen, there are a variety of known amplification methods and a variety of conditions under which these methods are conducted to achieve exponential amplification.

Linear amplification of nucleic acids or polynucleotides—any method that results in the formation of one or more copies of only the complement of a nucleic acid or polynucleotide molecule, usually a nucleic acid or polynucleotide analyte, present in a medium. Thus, one difference between linear amplification and exponential amplification is that the latter produces copies of the polynucleotide whereas the former produces only the complementary strand of the polynucleotide. In linear amplification the number of complements formed is, in principle, directly proportional to the time of the reaction as opposed to exponential amplification wherein the number of copies is, in principle, an exponential function of the time or the number of temperature cycles.

Ancillary Materials—various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

In accordance with one embodiment of the present invention for the detection of a target polynucleotide sequence, an oligonucleotide is reversibly hybridized with a target polynucleotide sequence within a polynucleotide analyte, under isothermal conditions. The target polynucleotide sequence serves as a template for addition of at least one nucleotide, usually from 1 to 10 nucleotides, preferably, 1 to 5 nucleotides, more preferably, 1, 2 or 3 nucleotides, which may be the same or different, to the 3'-terminus of the oligonucleotide to provide an extended oligonucleotide. Generally, the number of nucleotides added is controlled by the number of different nucleoside triphosphates added to the reaction medium and by the length of the series of nucleotides, complementary to the added nucleotide triphosphates, that is in the template adjacent to the 5'-end of the sequence that binds to the oligonucleotide. In the present invention 1 to 3 different nucleoside triphosphates are employed. Such a situation provides a control on the number of nucleotides that add to the template under the isothermal conditions employed. It should be noted further that an extended oligonucleotide having more than about 5 additional nucleotides decreases the rate of addition of nucleotides using the present method. In general, as the length of the extended oligonucleotide increases, the ability of the resulting extended oligonucleotide to dissociate from the template at the isothermal temperature of the reaction is decreased. The nature of the nucleotide composition is also a factor such that addition of more G and/or C nucleotides, relative to A and/or T nucleotides, will reduce the overall number of nucleotides that can be added in order that the reaction can be carried out at isothermal temperature.

In this way a plurality of molecules of extended oligonucleotide are obtained each being a complement of the target polynucleotide sequence. Preferably, at least a 100-fold molar excess, more preferably, at least a 10000-fold molar excess, of extended oligonucleotide is obtained in the present method relative to the molar amount of the target polynucleotide sequence. The upper limit for the number of molecules of extended oligonucleotide that are formed depends on such factors as time of reaction, reaction conditions, enzyme activity, and so forth. The extended oligonucleotide only forms when the target polynucleotide sequence is present in the sample. Therefore, the presence of extended oligonucleotide signals the presence of the target polynucleotide sequence.

Such an embodiment of the method is depicted schematically in FIG. 1. Oligonucleotide OL is combined with polynucleotide analyte PA having target polynucleotide sequence TPS and with functioning deoxynucleoside triphosphates (dATP, dUTP and dGTP) and a polynucleotide polymerase (PP). In this embodiment three of the four generally recognized deoxynucleoside triphosphates are employed by way of example and not limitation. The term "functioning" means that the deoxynucleoside triphosphates support chain extension under appropriate extension conditions. It is within the purview of the present invention to use 1 to 3 of such different deoxynucleoside triphosphates and omit the remaining ones or to use, in place of the missing deoxynucleoside triphosphates, modified nucleoside triphosphates that, once incorporated by chain extension, do not support further chain extension, such as, e.g., dideoxynucleoside triphosphates. OL is about 10 to 80 nucleotides in length, preferably, 15 to 30 or more nucleotides in length. The OL must be able to hybridize with TPS and in this embodiment is 1 to 10 nucleotides shorter than TPS and is chosen so that the addition of no more than 1 to 10 nucleotides thereto results in EOL, an extended OL that is the same length as TPS.

As can be seen with reference to FIG. 1, OL hybridizes with TPS to give duplex I. The hybridization is carried out under isothermal conditions at a temperature at which OL and EOL are reversibly hybridized with TPS. OL in duplex I is extended in the presence of the deoxynucleoside triphosphates, and polynucleotide polymerase PP and nucleotides are added up to the first nucleotide in the TPS that is complementary to the missing deoxynucleoside triphosphate, (dCTP in this example). At that point the extension of OL ceases. No more than three different nucleotides are added to OL to give extended OL (EOL), which is the complement of TPS. The isothermal conditions are chosen such that equilibrium exists between duplex I and its single stranded counterparts. Accordingly, the denatured form of duplex I, after formation of EOL, has free EOL, PA and OL. OL then rehybridizes with TPS of PA and the reaction in which EOL is formed is repeated. The reaction is allowed to continue until a sufficient number of molecules of the complement of the TPS, namely EOL, are formed to permit detection of EOL as an indicator of the presence of the polynucleotide analyte. In this way the addition of nucleotides to the 3'-terminus of OL is template dependent and related to the presence of the polynucleotide analyte.

The method is conducted for a time sufficient to achieve the desired number of molecules of extended oligonucleotide. Usually, a sufficient number of molecules for detection can be obtained where the time of reaction is from about 10 minutes to 24 hours, preferably, 10 minutes to 2 hours. As a matter of convenience it is usually desirable to minimize the time period as long as the requisite number of molecules of extended oligonucleotide is achieved.

Detection is facilitated in a number of ways. For example, a binder of EOL, such as streptavidin or a nucleotide sequence that hybridizes with EOL, can be used. One of either the oligonucleotide OL or a deoxynucleoside triphosphate, or both, can be labeled with a reporter molecule such as a receptor or a ligand, a small organic molecule or detectible label, a polynucleotide sequence, a protein including enzymes, a support, intercalation dye and the like and/or the deoxynucleoside triphosphate can be labeled with a small organic molecule ligand or detectible label including a fluorophor, chemiluminescer, radiolabel, sensitizer, metal chelate, dye, etc. Usually detection of the EOL will be carried out by detecting the association of the OL sequence or its reporter molecule with a label on the added nucleotides. Detection can be carried out by any standard method such as binding the EOL to a support and detecting the reporter molecule or label on the support or detecting the proximity of the reporter molecule and label by a homogeneous method such as an induced luminescence immunoassay referred to below or fluorescence energy transfer. Alternatively the EOL can be detected by template dependent ligation to a single stranded polynucleotide using a polynucleotide template that does not support ligation of the OL.

In a preferred embodiment only one deoxynucleoside triphosphate is used, which is labeled, and the label is incorporated into OL' to form EOL' during the reaction. Such an approach is shown in FIG. 2, where dATP is labeled as indicated by an asterisk. In this embodiment OL' and PA' are in reversible equilibrium with duplex I'. It should be noted that OL' in FIG. 2 contains a portion SOL that does not hybridize with TPS' of PA' and which can serve as a reporter molecule.

One method for detecting nucleic acids is to employ nucleic acid probes. Other assay formats and detection formats are disclosed in U.S. patent applications Ser. Nos. 07/229,282 and 07/399,795 filed Jan. 19, 1989, and Aug. 29, 1989, respectively, U.S. patent application Ser. No. 07/555,323 filed Jul. 19, 1990, U.S. patent application Ser. No. 07/555,968 and U.S. patent application Ser. No. 07/776,538 filed Oct. 11, 1991, which have been incorporated herein by reference.

Examples of particular labels or reporter molecules and their detection can be found in U.S. patent application Ser. No. 07/555,323 filed Jul. 19, 1990, the relevant disclosure of which is incorporated herein by reference.

Detection of the signal will depend upon the nature of the signal producing system utilized. If the label or reporter group is an enzyme, additional members of the signal producing system include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule, the medium can be irradiated and the fluorescence determined. Where the label is a radioactive group, the medium can be counted to determine the radioactive count.

The present method has application where the target polynucleotide sequence is DNA or RNA.

The extension of an oligonucleotide in accordance with the present invention is generally carried out using a nucleotide polymerase, nucleoside triphosphates or analogs thereof capable of acting as substrates for the polynucleotide polymerase and other materials and conditions required for enzyme activity such as a divalent metal ion (usually magnesium), pH, ionic strength, organic solvent (such as formamide), and the like.

The polynucleotide polymerase is usually a reverse transcriptase when the target polynucleotide sequence is RNA and a DNA polymerase when the target polynucleotide sequence is DNA. The polynucleotide polymerase is generally present in an amount sufficient to cause addition of nucleotides to the oligonucleotide to proceed at least twenty percent as rapidly as the maximum rate achievable with excess enzyme, preferably, at least 50% of the maximum rate. The concentration of the polynucleotide polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

The oligonucleotide that is extended by the enzyme is usually in large excess, preferably, $10^{-9}$M to $10^{-5}$M, and is used in an amount that maximizes the overall rate of its extension in accordance with the present invention wherein the rate is at least 10%, preferably, 50%, more preferably, 90%, of the maximum rate of reaction possible. Concentrations of the oligonucleotide that produce rates lower than 50% of the maximum rate may be employed to minimize potential interference by the oligonucleotide in the detection of the product(s) produced in accordance with the present invention. Usually, the concentration of the oligonucleotide is 0.1 nanomolar to 1 millimolar, preferably, 1 nanomolar to 10 micromolar. It should be noted that increasing the concentration of the oligonucleotide causes the reaction rate to approach a limiting value that depends on the oligonucleotide sequence, the temperature, the concentration of the target polynucleotide sequence and the enzyme concentration. For many detection methods very high concentrations of the oligonucleotide may make detection more difficult. The amount of oligonucleotide is at least as great as the number of molecules of product desired and is usually $10^{-16}$ to $10^{-4}$ moles per sample, where the sample is 1–1,000 μL. Usually, the oligonucleotide is present in at least $10^{-9}$M, preferably $10^{-7}$M, and more preferably at least about $10^{-6}$M. Preferably, the concentration of the oligonucleotide is substantially in excess over, preferably at least 100 times greater than, the concentration of the target polynucleotide sequence.

The amount of the target polynucleotide sequence that is to be amplified can be as low as one or two molecules in a sample but generally may vary from about $10^2$ to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$M.

In carrying out the methods in accordance with the present invention, an aqueous medium is employed. Other polar solvents may also be employed as cosolvents, usually oxygenated organic solvents of from 1–6, more usually from 1–4, carbon atoms, including formamide, DMSO, and the like. Usually these cosolvents, if used, are present in less than about 70 weight percent, more usually in less than about 30 weight percent.

The pH for the medium is usually in the range of about 4.5 to 9.5, more usually in the range of about 5.5–8.5, and. preferably in the range of about 6–8. The pH and temperature are chosen so as to achieve the reversible hybridization or equilibrium state under which extension of an oligonucleotide occurs in accordance with the present invention. In some instances, a compromise is made in the reaction parameters in order to optimize the speed, efficiency, and specificity of these steps of the present method. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

As mentioned above the reaction in accordance with the present invention is carried out under isothermal conditions. The reaction is generally carried out at a temperature that is near the melting temperatures of the oligonucleotide:target polynucleotide sequence and the extended oligonucleotide-:target polynucleotide sequence complexes. Accordingly, the temperature employed depends on a number of factors. Usually, for extension of the oligonucleotide in accordance with the present invention, the temperature is about 35° C. to 90° C. depending on the length and sequence of the target polynucleotide sequence. It will usually be desired to use a relatively high temperature of 60° C. to 85° C. to provide for a high rate of reaction. Usually, the temperature used is be between 15° C. below and 15° C. above the melting temperature of the oligonucleotide: target polynucleotide sequence complex. The amount of the extended molecules formed depends on the incubation time and temperature.

The particular temperature utilized also varies depending on the salt concentration, pH, solvents used, and the length of and composition of the target polynucleotide sequence as well as the oligonucleotide as mentioned above. Thus, for example, the oligonucleotide can be designed such that there are one or more portions having nucleotides that are not hybridizable or complementary to the target polynucleotide sequence or to corresponding nucleotides in the target polynucleotide sequence. This approach offers the ability to operate at lower temperature for a given number of nucleotide pairs. The specificity of the reaction can be maintained at a high level without requiring temperatures that exceed the optimum functioning temperature of the nucleotide polymerase. Examples of such embodiments, by way of illustration and not limitation, are shown in FIGS. 3–5. In FIG. 3 oligonucleotide OL has a portion POL that is not hybridizable with TPS. In FIG. 4 oligonucleotide OL is not hybridizable with portion PTPS of TPS. In FIG. 5 oligonucleotide OL has a portion POL that is not hybridizable with portion PTPS of TPS. The number of nucleotides in such portions above are about 1 to 30, preferably, 5 to 25. The number of nucleotides flanking such portions that are hybrizable to TPS or OL are about 6 to 24 nucleotides on each side of such portions, preferably 8 to 18.

The concentration of the deoxynucleoside triphosphates in the medium can vary widely; preferably, these reagents are present in an excess amount. The deoxynucleoside triphosphates are usually present in $10^{-6}$ to $10^{-2}$M, preferably $10^{-5}$ to $10^{-3}$M.

The order of combining of the various reagents to form the combination may vary from wholly or partially sequential to simultaneous or concomitant. Generally, the target polynucleotide sequence as part of the polynucleotide analyte is obtained from a sample containing such polynucleotide analyte, which may be pretreated as mentioned above. Generally, the target polynucleotide sequence is combined with the oligonucleotide. A pre-prepared combination of deoxynucleoside triphosphates and polynucleotide polymerase may be included in the prepared combination or may be added subsequently. However, simultaneous addition of all of the above, as well as other step-wise or sequential orders of addition, may be employed.

The concentration and order of addition of reagents and conditions for the method are governed generally by the desire to maximize the number of molecules of extended oligonucleotide and the rate at which such molecules are formed.

The final concentration of each of the reagents is normally determined empirically to optimize the sensitivity of the assay over the range of interest. The primary consideration in an assay is that a sufficient number of molecules of extended oligonucleotide be produced so that such molecules can be readily detected and provide an accurate determination of the target polynucleotide sequence.

Another embodiment of the present invention is a method of forming an oligonucleotide having at least two labels. A combination is provided comprising a catalytic amount of a target polynucleotide sequence, a nucleotide polymerase, a first-labeled deoxynucleoside triphosphate, a second-labeled oligonucleotide that is complementary to a portion of the target polynucleotide sequence. The combination is treated under isothermal conditions such that the labeled oligonucleotide reversibly hybridizes to the target polynucleotide sequence to form a duplex and the labeled deoxynucleoside triphosphate becomes linked to the labeled oligonucleotide. In an assay for a target polynucleotide sequence the oligonucleotide is detected by examining for the presence of both labels within the same molecules. The presence of the oligonucleotide having both labels is an indication of the presence of the target polynucleotide sequence.

An example of such an embodiment is depicted schematically in FIG. 6. In this embodiment an oligonucleotide OL" is employed that has a label (**) that is directly detectable or is a ligand such as a small molecule, e.g., biotin, fluorescein or a second oligonucleotide, for example (dT)40. The deoxynucleoside triphosphates employed include a labeled deoxynucleoside triphosphate (dNTP1*). In the presence of the nucleotide polymerase and dNTP1*, OL" is extended along the polynucleotide analyte PA" to add one or more of the labeled nucleotide to give extended OL" (EOL"). EOL" is the complement of TPS". Under appropriate isothermal conditions an equilibrium is present wherein duplex I" is in equilibrium with single stranded PA" and EOL", the product oligonucleotide. EOL" now contains both labels * and **. EOL" dissociates from PA" thereby freeing PA" to be bound by another molecule of OL". The isothermal conditions are appropriately chosen such that PA" hybridizes with another molecule of OL" to give duplex I" and the above described reactions occur again. The time of the reaction is chosen to achieve a sufficient number of molecules of the complement of the TPS", namely, EOL", to permit detection of the polynucleotide analyte.

Detection of product oligonucleotide containing two labels can be by any method. For example, one can use a method that involves modulation by the association of the two labels. Sandwich ligand binding assays can be employed such as, for example, an ELISA assay or an enzyme channeling immunoassay in which receptors for the labels are used. Alternatively, a receptor for one of the two labels can be used to capture the product oligonucleotide where the other label can be directly detected such as, for example, by fluorescence. In a particularly attractive approach one label is a photosensitizer and the other label permits capture of the product oligonucleotide on a receptor-coated surface, such as, e.g., beads that form a suspension in a liquid medium, where the surface contains a chemiluminescent reagent. Following addition of the surface and incubation for a period sufficient for the product oligonucleotide to bind to the surface, the suspension is irradiated with light that can be absorbed by the photosensitizer and not by the chemiluminescent reagent. The light is then turned off and the luminescence of the surface is a measure of the presence of polynucleotide analyte.

The labeled molecule can be detected by any standard binding assay, either without separation (homogeneous) or with separation (heterogeneous) of any of the assay components or products. Homogeneous immunoassays are exemplified by enzyme multiplied immunoassay techniques ("EMIT") disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59 to column 23, line 25; enzyme channeling techniques such as those disclosed in Maggio, et al., U.S. Pat. No. 4,233,402, column 6, line 25 to column 9, line 63; and other enzyme immunoassays such as the enzyme linked immunosorbant assay ("ELISA") are discussed in Maggio, E. T. supra. Exemplary of heterogeneous assays are the radioimmunoassay, disclosed in Yalow, et al., J. Clin. Invest. 39:1157 (1960). The above disclosures are all incorporated herein by reference. For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. A typical non-competitive assay is a sandwich assay disclosed in David, et al., U.S. Pat. No. 4,486,530, column 8, line 6 to column 15, line 63, incorporated herein by reference.

Another binding assay approach involves the induced luminescence immunoassay referred to in U.S. Ser. No. 07/704,569, filed May 22, 1991, entitled "Assay Method Utilizing Induced Luminescence", which disclosure is incorporated herein by reference.

Another embodiment of the present invention is a method for detecting a mutation in a target polynucleotide sequence. In the method an oligonucleotide is reversibly hybridized with a target polynucleotide sequence suspected of having a mutation in the presence of a nucleotide polymerase under isothermal conditions. The target polynucleotide sequence serves as a template for addition of at least one nucleotide, usually from 1 to 10 nucleotides, preferably, 1 to 5 nucleotides, more preferably, 1, 2 or 3 nucleotides to the 3'-terminus of the oligonucleotide to provide an extended oligonucleotide wherein at least a 100-fold molar excess of the extended oligonucleotide is obtained relative to the molar amount of the target polynucleotide sequence. One of the nucleotides contains a label. The presence of the label in the extended oligonucleotide is determined, the presence thereof indicating the presence of the mutation in the target polynucleotide sequence.

Such an embodiment is depicted in FIG. 7. TPS' is suspected of having a point mutation. An oligonucleotide OL' is prepared to hybridize with a portion of TPS' up to the point of the suspected mutation (indicated by an arrow in FIG. 7), which is immediately 5' of the last nucleotide of TPS' to which OL' is hybridized. If the mutation is suspected to be a nucleotide T, a single labeled nucleotide, dA*TP, is included in the reaction mixture along with PP. As can be seen with reference to FIG. 7, OL' hybridizes with TPS' to give duplex I'. The hybridization is carried out under isothermal conditions at a temperature at which OL' and EOL' are reversibly hybridized with TPS'. OL' in duplex I' is extended to add labeled nucleotide A* only if the suspected mutation is; present in TPS'. If the suspected mutation T is not present, the extension of OL' does not occur and the label is not incorporated into EOL'. If the mutation is present, the extension of OL ceases after A* is added. As above, the isothermal conditions are chosen such that equilibrium exists between duplex I' and its single stranded counterparts. Accordingly, the denatured form of duplex I, after formation of EOL' if the mutation is present, has free EOL', PA' and OL'. OL' then rehybridizes with TPS' of PA' and the reaction in which EOL' is formed is repeated. The reaction is allowed to continue until a sufficient number of molecules of EOL' are formed to permit detection of EOL' as an indicator of the presence of the mutation in the target polynucleotide sequence TPS'.

A variant of the above is depicted in FIG. 8. In this embodiment two nucleotides are employed. One of the nucleotides is unlabeled, namely, dATP, and is complementary to the nucleotide in TPS', namely, T, suspected of being mutated (indicated by an arrow in FIG. 8). The other of the nucleotides contains a label, namely, dC*TP, and is complementary to the nucleotide, namely, G, which is 5' of and immediately adjacent to the nucleotide suspected of being mutated. OL' hybridizes with TPS' to give duplex I'. The hybridization is carried out under isothermal conditions at a temperature at which OL' and EOL' are reversibly hybridized with TPS'. OL' in duplex I' is extended to add labeled nucleotide C* and nucleotide A only if the suspected mutation is present in TPS'. If the suspected mutation T is not present, the extension of OL' does not occur and the label is not incorporated into EOL'. If the mutation is present, the extension of OL ceases after C* is added.

As a matter of convenience, predetermined amounts of reagents employed in the present invention can be provided in a kit in packaged combination. A kit can comprise in packaged combination (a) one to three nucleoside triphosphates at least one of which is comprised of or convertible to a label, (b) an oligonucleotide complementary at its 3'-end to a polynucleotide to be detected, (c) a nucleotide polymerase and (d) means for detecting the label of the deoxynucleoside triphosphate when the label is bound to the oligonucleotide. In one embodiment of the above kit the oligonucleotide is an oligodeoxynucleotide.

The above kits can further include members of a signal producing system and also various buffered media, some of which may contain one or more of the above reagents. The above kits can also include a written description of one or more of the methods in accordance with the present invention for detecting a target polynucleotide sequence, which methods are described above.

The relative amounts of the various reagents in the kits can be varied widely to provide for concentrations of the reagents which substantially optimize the reactions that need to occur during the present method and to further substantially optimize the sensitivity of any assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit.

EXAMPLES

The invention is demonstrated further by the following illustrative examples. Temperatures are in degrees centigrade (° C.) and parts and percentages are by weight, unless otherwise indicated.

The following abbreviations are used herein: DTT—dithiothreitol (from Sigma Chemical Company, St. Louis, Mo.).

Example 1

A single stranded target DNA ($10^8$ molecules) (M13mp18 from 'GIBCO BRL, Gaithersburg, Md.) was combined with a $5'^{32}$P-labeled oligonucleotide probe (labeled probe) (10 µM) 5'GAC-GGC-CAG-TGA-ATT-CGA-GC 3' (SEQ ID NO:1), synthesized on a Pharmacia Gene Assembler, Pharmacia Biotech, Piscataway, N.J., 100 µM TTP and 2.5 units of Pfu exo minus DNA polymerase (from Stratagene, San Diego, Calif.) in 50 µL of buffer (10 mM Tris-HCl, pH 8.8, 50 mM KCl, 1.5 mM $MgCl_2$, 0.1% Triton X-100, 7.5 mM DTT). The reaction mixture was incubated at 74° C. and accumulation of product, namely, 5' GAC-GGC-CAG-TGA-ATT-CGA-GCT 3' (SEQ ID NO:2), was determined by visualization using autoradiography following polyacrylamide gel electrophoresis (PAGE).

The extent of amplification was determined by liquid scintillation spectrometry of excised reaction product. A $1.5 \times 10^4$ fold amplification was observed.

In the above examples a polymerase facilitated the addition of a single modified base to the 3'-end of an oligonucleotide probe in a template directed manner, i.e., when the probe was annealed to the target DNA. Amplification occurred at a constant temperature when the melting temperature (Tm) of the modified or labeled probe was very close to that of the original, unmodified probe. Reactions carried out at or near the Tm of the probe allowed for continuous annealing and dissociation of the probe (modified and unmodified) to the target. Once modified by the enzyme, the probe dissociated from the target allowing an unmodified probe (in molar excess in this example) to anneal. Over a period of time an accumulation of a specifically labeled oligonucleotide probe was achieved.

Example 2

The reaction protocol followed in EXAMPLE 1 was repeated with other oligonucleotide probes and with biotin-16-dUTP in place of TTP. The following summarizes the reagents and conditions and the results obtained:
A) Control:
5'TCA-CGA-CGT-TGT-AAA-ACG-ACG-GCC-ACT-GAA 3' (SEQ ID NO:3)
Conditions: buffer, oligo nucleotide probe and target DNA (described previously) at equimolar concentrations (0.4 picomoles/50 µL reaction); incubated at 74° C. for 30 minutes with 2.5 units Pfu exo minus DNA polymerase and 50 $\mu$M or 100 $\mu$M Biotin-16-dUTP (Boehringer Mannheim, Indianapolis, Ind.)

These short incubations were conducted to see if the enzyme (Pfu) would efficiently add the Biotin-16-dUTP to the 3' end of the above oligo. The modified base was added efficiently as determined by PAGE analysis (described previously).

B) Reactions:

5' CGT-GGG-AAC-AAA-CGG-CGG-AT 3' (SEQ ID NO:4)

Conditions: buffer and volume as described above; target DNA (same as above) concentration was varied: $10^{11}$ to $10^7$ molecules; oligonucleotide probe concentration was varied: 0.01 to 100 $\mu$M; temperature was varied: 74° C. to 82° C.; Pfu exo minus DNA polymerase (Pfu exo-) concentration was varied: 2.5 to 10 units/reaction. Incubations were carried out up to 5 hours. All reactions were conducted in the presence of 100 $\mu$M TTP.

Results: With $10^8$ targets for 5 hours at 74° C., 50 $\mu$L reaction, 100 $\mu$M TTP the following results were obtained:

a) 1 $\mu$M oligonucleotide; 2.5 units Pfu exo-: $8 \times 10^3$ fold amplification b) 1 $\mu$M oligonucleotide; 5.0 units Pfu exo-: $4.5 \times 10^3$ fold amplification c) 10 $\mu$M oligonucleotide; 2.5 units Pfu exo-: $1.5 \times 10^4$ fold amplification d) 10 $\mu$M oligonucleotide; 5.0 units Pfu exo-: $1.4 \times 10^4$ fold amplification No significant increase in amplification was detected as enzyme concentration was increased. No significant amplification was detected at temperatures between 76° C. and 82° C., presumably above the melting temperature (Tm) of the oligonucleotide:target polynucleotide sequence and the extended oligonucleotide:target polynucleotide sequence complexes.

The above experiments demonstrate that a detectable amplification product is generated from the 3'-end of an oligonucleotide probe in a target-specific manner at a single temperature using an enzyme having nucleotide polymerase activity. The reactions are carried out at temperatures very close to the Tm of the duplex containing the modified probe.

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the following claims.

---

What is claimed is:

1. A method for detecting a target polynucleotide sequence, which comprises:
(a) reversibly hybridizing an oligonucleotide with a target polynucleotide sequence in the presence of a nucleotide polymerase and 1 to 3 different nucleoside triphosphates under isothermal conditions wherein said target polynucleotide sequence serves as a template for addition of at least one nucleotide to the 3'-terminus of said oligonucleotide under said isothermal conditions to provide an extended oligonucleotide wherein at least a 100-fold molar excess of said extended oligonucleotide is obtained relative to the molar amount of said target polynucleotide sequence and wherein said isothermal conditions comprise an isothermal temperature within 15° C. below and 15° C. above the melting temperature of the oligonucleotide:target polynucleotide sequence complex and wherein said isothermal conditions exclude fluctuation in temperature referred to as thermal cycling, and
(b) detecting the presence of said extended oligonucleotide, the presence thereof indicating the presence of said target polynucleotide sequence.

2. The method of claim 1 wherein at least said nucleotide has a label.

3. The method of claim 1 wherein said oligonucleotide has a label.

4. The method of claim 1 wherein only 1 nucleotide is added.

5. The method of claim 1 wherein said target polynucleotide sequence is DNA.

6. A method for detecting a target polynucleotide sequence, said method comprising:
(a) providing in combination a medium suspected of containing said target polynucleotide sequence, a molar excess, relative to the suspected concentration of said target polynucleotide sequence, of an oligonucleotide capable of hybridizing with said target polynucleotide sequence, 1 to 3 different nucleoside triphosphates and a nucleotide polymerase,
(b) reversibly hybridizing under isothermal conditions said target polynucleotide sequence and said oligonucleotide, wherein said oligonucleotide is extended under said isothermal conditions at its 3-end to produce an amount of an extended oligonucleotide that is at least 100 times the molar amount of said target polynucleotide sequence, wherein said isothermal conditions comprise an isothermal temperature within 15° C. below and 15° C. above the melting temperature of the oligonucleotide:target polynucleotide sequence complex and wherein said isothermal temperature is a constant temperature with a variance of ±2° C., and
(c) detecting the presence of said extended oligonucleotide, the presence thereof indicating the presence of said target polynucleotide sequence.

7. The method of claim 6 wherein at least one of said nucleoside triphosphates has a label.

8. The method of claim 7 wherein said oligonucleotide has a label.

9. The method of claim 6 wherein only 1 nucleoside triphosphate is added.

10. The method of claim 7 wherein said label is selected from the group consisting of members of specific binding pairs, dyes, fluorescent molecules, chemiluminescers, coenzymes, enzyme substrates and radioactive groups.

11. The method of claim 6 wherein said target polynucleotide sequence is DNA.

12. The method of claim 6 wherein said nucleoside triphosphates are selected from the group consisting of dUTP, dITP, dATP, dCTP and dGTP and dideoxynucleoside triphosphates.

13. A method for detecting a DNA analyte, said method comprising:
  (a) providing in combination a medium suspected of containing said DNA analyte, an oligonucleotide capable of hybridizing with said DNA analyte, 1 to 3 different nucleoside triphosphates and a template dependent DNA polymerase,
  (b) reversibly hybridizing said DNA analyte and said oligonucleotide under isothermal conditions, wherein said oligonucleotide is extended at its 3-terminus under said isothermal conditions to produce at least a 100-fold excess, relative to said DNA analyte, of an extended oligonucleotide, wherein said isothermal conditions comprise an isothermal temperature within 15° C. below and 15° C. above the melting temperature of the oligonucleotide:DNA analyte complex and wherein said isothermal temperature is a constant temperature with a variance of ±2° C. and
  (c) detecting the presence of said extended oligonucleotide, the presence thereof indicating the presence of said DNA analyte.

14. The method of claim 13 wherein said oligonucleotide has a substituent that facilitates separation of said oligonucleotide from said medium.

15. The method of claim 13 wherein said oligonucleotide has a label.

16. The method of claim 13 wherein at least one of said nucleoside triphosphates has a label.

17. The method of claim 16 wherein said label is selected from the group consisting of members of specific binding pairs, dyes, fluorescent molecules, chemiluminescers, coenzymes, enzyme substrates, radioactive groups and small organic molecules.

18. The method of claim 15 wherein said label is selected from the group consisting of members of specific binding pairs, dyes, fluorescent molecules, chemiluminescers, coenzymes, enzyme substrates, radioactive groups and small organic molecules.

19. A method for detecting the presence of a target polynucleotide sequence, said method comprising:
  (a) forming, in relation to the presence of said target polynucleotide sequence, at least a 100-fold excess, relative to said target polynucleotide sequence, of an extended oligonucleotide having at least two labels wherein during said forming an oligonucleotide is reversibly hybridized under isothermal conditions with said target polynucleotide sequence in the presence of a nucleotide polymerase and 1 to 3 different nucleoside triphosphates, wherein said target polynucleotide sequence serves as a template for addition of at least one nucleotide to the 3-end of said oligonucleotide under said isothermal conditions to provide an extended oligonucleotide and wherein one of said labels is part of said nucleotide and the other of said labels is part of said oligonucleotide and wherein said isothermal conditions comprise an isothermal temperature within 15° C. below and 15° C. above the melting temperature of the oligonucleotide:target polynucleotide sequence complex and wherein said isothermal conditions exclude fluctuation in temperature referred to as thermal cycling and
  (b) detecting both of said labels as an indication of the presence of said oligonucleotide, the presence thereof indicating the presence of said target polynucleotide sequence.

20. A method of forming an oligonucleotide having at least two labels, said method comprising the steps of:
  (a) providing in combination a catalytic amount of a target polynucleotide, a nucleotide polymerase, a first-labeled deoxynucleoside triphosphate, and a second-labeled oligonucleotide that is complementary to at least a portion of said target polynucleotide,
  (b) treating said combination under isothermal conditions such that said second-labeled oligonucleotide reversibly hybridizes to said target polynucleotide to form a duplex and said first-labeled deoxynucleoside triphosphate becomes linked to said labeled oligonucleotide under said isothermal conditions, wherein said isothermal conditions comprise an isothermal temperature within 15° C. below and 15° C. above the melting temperature of the oligonucleotide:target polynucleotide complex and wherein said isothermal temperature is a constant temperature with a variance of ±2° C.

21. A method for detecting a mutation in a target polynucleotide sequence, which comprises the steps of:
  (a) reversibly hybridizing an oligonucleotide with a target polynucleotide sequence suspected of having said mutation in the presence of a nucleotide polymerase under isothermal conditions in the presence of a nucleotide polymerase and 1 to 3 different nucleoside triphosphates wherein said target polynucleotide sequence serves as a template for addition of at least one nucleotide to the 3'-terminus of said oligonucleotide under said isothermal conditions to provide an extended oligonucleotide wherein at least a 100-fold molar excess of said extended oligonucleotide is obtained relative to the molar amount of said target polynucleotide sequence, wherein said nucleotide contains a label and wherein said isothermal conditions comprise an isothermal temperature within 15° C. below and 15° C. above the melting temperature of the oligonucleotide:target polynucleotide sequence complex and wherein said isothermal temperature is a constant temperature with a variance of ±2° C. and
  (b) detecting the presence of said label in said extended oligonucleotide, the presence thereof indicating the presence of said mutation in said target polynucleotide sequence.

22. The method of claim 21 wherein said target polynucleotide sequence is DNA.

23. The method of claim 21 wherein one nucleotide is added to said oligonucleotide, said nucleotide being complementary to the nucleotide suspected of being mutated.

* * * * *

UNITED STATES PATENT AND TRADEMARK OFFICE
CERTIFICATE OF CORRECTION

PATENT NO. : 5,882,867
DATED : March 16, 1999
INVENTOR(S) : Edwin F. Ullman, et. al.

It is certified that error appears in the above-indentified patent and that said Letters Patent is hereby corrected as shown below:

Column 4, Line 63: Delete "106" and insert --$10^6$--.

Column 10, Line 5: Delete "refers to one or more nucleotides, including the terminal"

Column 17, Line 50: Delete "$10^{-4}$" and insert --$10^{-8}$--.

Signed and Sealed this

Thirtieth Day of November, 1999

Attest:

Q. TODD DICKINSON

Attesting Officer

Acting Commissioner of Patents and Trademarks